United States Patent
Piper

(10) Patent No.: US 10,458,945 B2
(45) Date of Patent: Oct. 29, 2019

(54) APPARATUS AND METHODS FOR ION SEPARATION, ESPECIALLY IMS, USING AN ION SHUTTER

(71) Applicant: Smiths Detection-Watford Limited, Hertfordshire (GB)

(72) Inventor: Lee James Piper, Hertfordshire (GB)

(73) Assignee: SMITHS DETECTION—WATFORD LIMITED, Hertfordshire (GB)

( * ) Notice: Subject to any disclaimer, the term of this patent is extended or adjusted under 35 U.S.C. 154(b) by 0 days.

(21) Appl. No.: 15/748,882

(22) PCT Filed: Jul. 29, 2016

(86) PCT No.: PCT/GB2016/052360
§ 371 (c)(1),
(2) Date: Jan. 30, 2018

(87) PCT Pub. No.: WO2017/017479
PCT Pub. Date: Feb. 2, 2017

(65) Prior Publication Data
US 2018/0224400 A1     Aug. 9, 2018

(30) Foreign Application Priority Data
Jul. 30, 2015    (GB) .................................. 1513472.9

(51) Int. Cl.
*G01N 27/64*     (2006.01)
*H01J 49/40*     (2006.01)
(Continued)

(52) U.S. Cl.
CPC .......... *G01N 27/622* (2013.01); *H01J 49/004* (2013.01); *H01J 49/025* (2013.01); *H01J 49/061* (2013.01); *H01J 49/062* (2013.01)

(58) Field of Classification Search
CPC .... G01N 27/622; G01N 27/624; G01N 27/64; G01N 27/447; G01N 27/68; H01J 49/061;
(Continued)

(56) References Cited

U.S. PATENT DOCUMENTS

| 8,173,959 B1 * | 5/2012 | Boumsellek | G01N 27/622 250/281 |
| 8,866,073 B2 * | 10/2014 | Goedecke | H01J 49/427 250/282 |

(Continued)

FOREIGN PATENT DOCUMENTS

| CN | 104392889 A | 3/2015 |
| EP | 2325865 A1 | 5/2011 |
| WO | 2007080376 A1 | 7/2007 |

OTHER PUBLICATIONS

Kurnin, Igor V. et al., "Bradbury-Nielsen gate electrode potential switching modes optimizing the ion packet time width in an ion mobility spectrometer", Int. J. Ion Mobil. Spec. (2014) 17:79-85.
(Continued)

Primary Examiner — David A Vanore
(74) Attorney, Agent, or Firm — Kevin E. West; Advent, LLP

(57) ABSTRACT

The disclosure relates to methods and apparatus for ion separation, for example using time of flight and ion mobility spectrometry. Ion shutters for use in IMS cells and to methods of operating them are also disclosed. The shutter includes a first shutter electrode and a second shutter electrode. A barrier voltage between these two electrodes is controlled to open and close the shutter to allow ions of interest to pass through the shutter in a drift direction. The control involves varying both: (a) the voltage of the first shutter electrode; and (b) the voltage of the second shutter electrode.

14 Claims, 6 Drawing Sheets

(51) Int. Cl.
*G01N 27/62* (2006.01)
*H01J 49/06* (2006.01)
*H01J 49/00* (2006.01)
*H01J 49/02* (2006.01)

(58) Field of Classification Search
CPC ........ H01J 49/062; H01J 49/004; H01J 49/40; H01J 49/0031; H01J 49/065; H01J 49/4235; H01J 49/00; H01J 49/0027; H01J 49/36; H01J 49/0036; H01J 49/005; H01J 49/022; H01J 49/025; H01J 49/04; H01J 49/0422; H01J 49/0431; H01J 49/0495; H01J 49/105; H01J 49/145; H01J 49/403; H01J 49/4225; H01J 49/426; H01J 49/427; H01J 33/02; H01J 27/205; H01J 3/021; H01J 29/04; H05H 1/2406; H05H 2001/2412; H05H 2001/2468
USPC ....... 250/282, 281, 290, 283, 286, 287, 288, 250/294, 396 R, 397, 423 R
See application file for complete search history.

(56) References Cited

U.S. PATENT DOCUMENTS

| | | | | |
|---|---|---|---|---|
| 9,006,678 B2* | 4/2015 | Ivashin | ................... | H01J 31/04 250/423 R |
| 9,070,542 B2* | 6/2015 | Ivashin | ................ | H01J 49/105 |
| 9,123,515 B2* | 9/2015 | Fujita | .................... | H01J 49/062 |
| 9,147,565 B1* | 9/2015 | Goedecke | ............ | G01N 27/622 |
| 9,293,313 B2* | 3/2016 | Li | ......................... | H01J 49/061 |
| 9,778,224 B2* | 10/2017 | Kubelik | ................ | G01N 27/68 |
| 2003/0132379 A1* | 7/2003 | Li | ......................... | G01N 27/622 250/286 |
| 2004/0245452 A1* | 12/2004 | Bateman | .............. | G01N 27/622 250/287 |
| 2005/0109930 A1* | 5/2005 | Hill, Jr. | ................ | G01N 27/622 250/286 |
| 2005/0205775 A1* | 9/2005 | Bromberg | ........... | G01N 27/622 250/290 |
| 2006/0219889 A1* | 10/2006 | Shvartsburg | ......... | G01N 27/624 250/282 |
| 2008/0179515 A1* | 7/2008 | Sperline | ............... | G01N 27/622 250/290 |
| 2009/0302209 A1* | 12/2009 | Green | ................... | H01J 49/065 250/282 |
| 2009/0314935 A1* | 12/2009 | Hoyes | ................. | H01J 49/4235 250/283 |
| 2010/0032561 A1* | 2/2010 | Giles | ................... | H01J 49/4235 250/283 |
| 2010/0327157 A1* | 12/2010 | Green | ................... | H01J 49/065 250/282 |
| 2015/0108345 A1 | 4/2015 | Fujita | | |
| 2016/0163526 A1* | 6/2016 | Green | ................... | H01J 49/065 250/287 |
| 2016/0203967 A1* | 7/2016 | Atkinson | .............. | H01J 49/061 250/282 |
| 2017/0138904 A1* | 5/2017 | Ueno | .................... | G01N 27/447 |
| 2017/0241952 A1* | 8/2017 | Atkinson | ............. | G01N 27/622 |
| 2017/0248546 A1* | 8/2017 | Munro | ................. | G01N 27/622 |
| 2018/0224400 A1* | 8/2018 | Piper | ................... | G01N 27/622 |

OTHER PUBLICATIONS

Puton, Jaroslaw et al., "Modelling of penetration of ions through a shutter grid in ion mobility spectrometers", Sensor and Actuators B, 135 (2008) 116-121.
International Search Report dated Nov. 30, 2016 for PCT/GB2016/052360.
Combined Search and Examination Report dated Jun. 23, 2016 for GB Appln. No. 1513472.9.

* cited by examiner

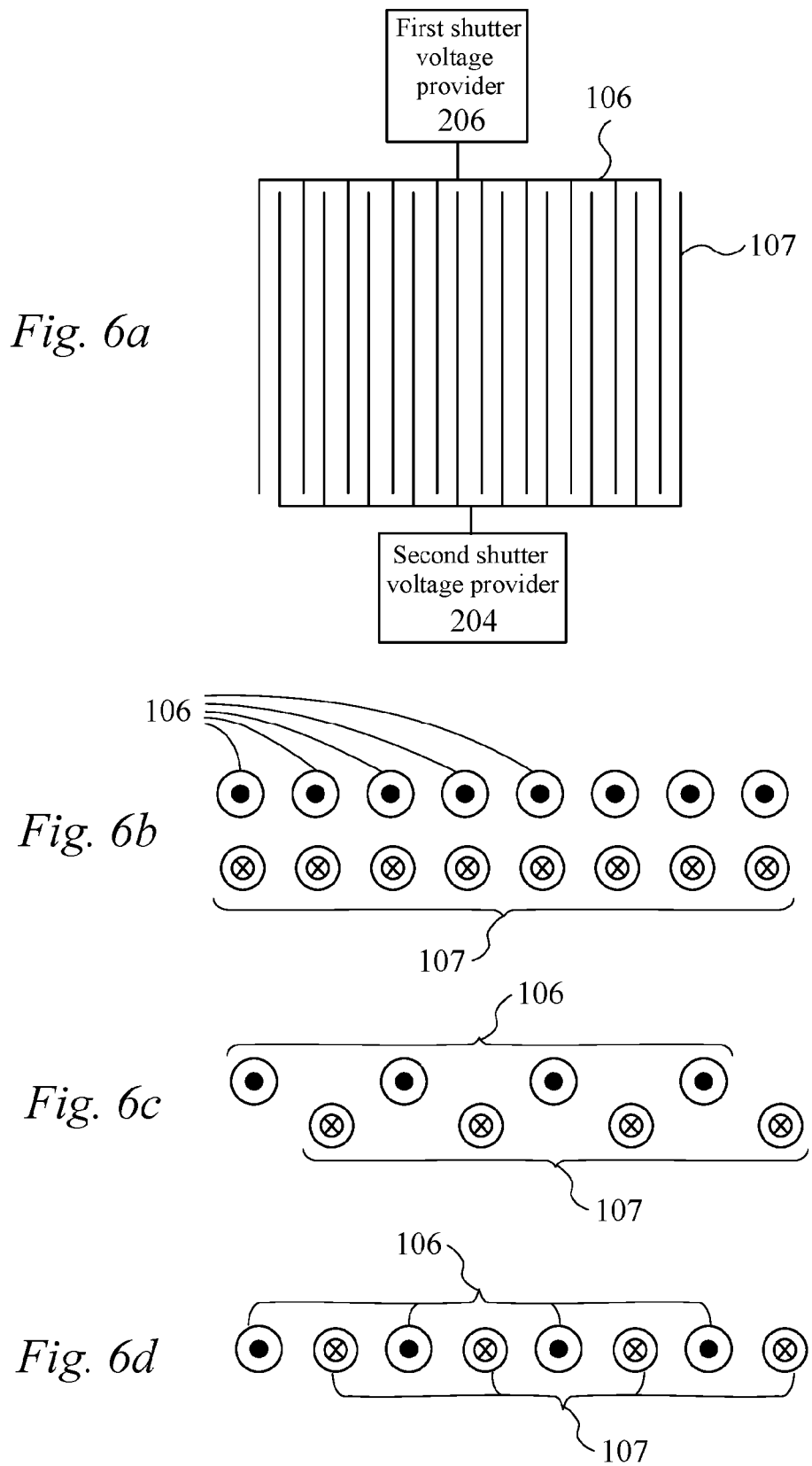

APPARATUS AND METHODS FOR ION SEPARATION, ESPECIALLY IMS, USING AN ION SHUTTER

FIELD OF INVENTION

The present disclosure relates to apparatus and methods, more particularly to methods and apparatus for ion separation, for example using time of flight spectrometry, and still more particularly to ion shutters for use in IMS cells and to methods of operating them.

BACKGROUND

Ion mobility spectrometers (IMS) can identify material from a sample of interest by ionising the material (e.g., molecules, atoms, and so forth) and measuring the time it takes the resulting ions to travel a known distance under a known electric field. Each ion's time of flight is associated with the ion's mobility. An ion's mobility relates to its mass and geometry. Therefore, by measuring the time of flight of an ion it is possible to infer its identity. These times of flight may be displayed graphically or numerically as a plasmagram.

Some IMS cells include detectors which collect ions to measure their time of flight so they can be identified, this may be done in the presence of a drift gas so that mobility effects can separate the ions. Some IMS cells may separate ions according to their time of flight so that ions having selected times of flight (implying a selected range of ion mobilities) can be provided to other detector instruments, such as mass spectrometers, for further analysis. One example of this technique is known as IMS-MS, in which an IMS cell is used as an ion filter to select ions from a sample. The selected ions are then provided to a mass spectrometer. In such ion identification or filtering methods, groups of ions can be released from a reaction region by opening an ion shutter and/or passed into an inlet of a mass spectrometer.

The reaction region of an IMS cell has a finite length, and in the time interval for which the shutter is held open, ions which may be distributed around the reaction region must travel (at least partially) across that reaction region to reach the shutter. The inventor in the present case has appreciated that this means that holding the shutter open only for a short interval reduces the number of slow moving ions that are able to travel through it in that interval. The inventor in the present case has recognised that this may reduce sensitivity of the detector to slow moving ions. After ions have passed through the shutter, their motion along the drift chamber is dependent upon the voltage profile in that drift chamber. He has further appreciated that the action of closing the shutter may modify the profile voltage near to the shutter. If so, the back of a group of ions in the drift chamber may experience a profile voltage different from that which the front of that group did when at that same position. The inventor concludes from this that this can retard or accelerate the ions at the back of the group relative to the rest of the group.

This leads him to believe that these factors may adversely affect the resolution and sensitivity of an IMS cell.

SUMMARY OF INVENTION

Aspects and embodiments of the invention are set out in the appended claims and aim to at least partially address problems such as those described above. These and other aspects and embodiments of the invention are also described herein.

BRIEF DESCRIPTION OF DRAWINGS

Embodiments will now be described, by way of example only, with reference to the accompanying drawings, in which:

FIG. 3 illustrates a method of operating an IMS cell and includes a set of schematic diagrams of IMS cells each with an illustration of a voltage profile along the IMS cell in which.

FIG. 6 shows a schematic diagram of ion shutter arrangements including a view facing the shutter along the drift direction (FIG. 6A), a section through three different possible shutter configurations perpendicular to the drift direction (FIG. 6B, FIG. 6C, and FIG. 6D).

In the drawings like reference numerals are used to indicate like elements.

SPECIFIC DESCRIPTION

Figure 1:
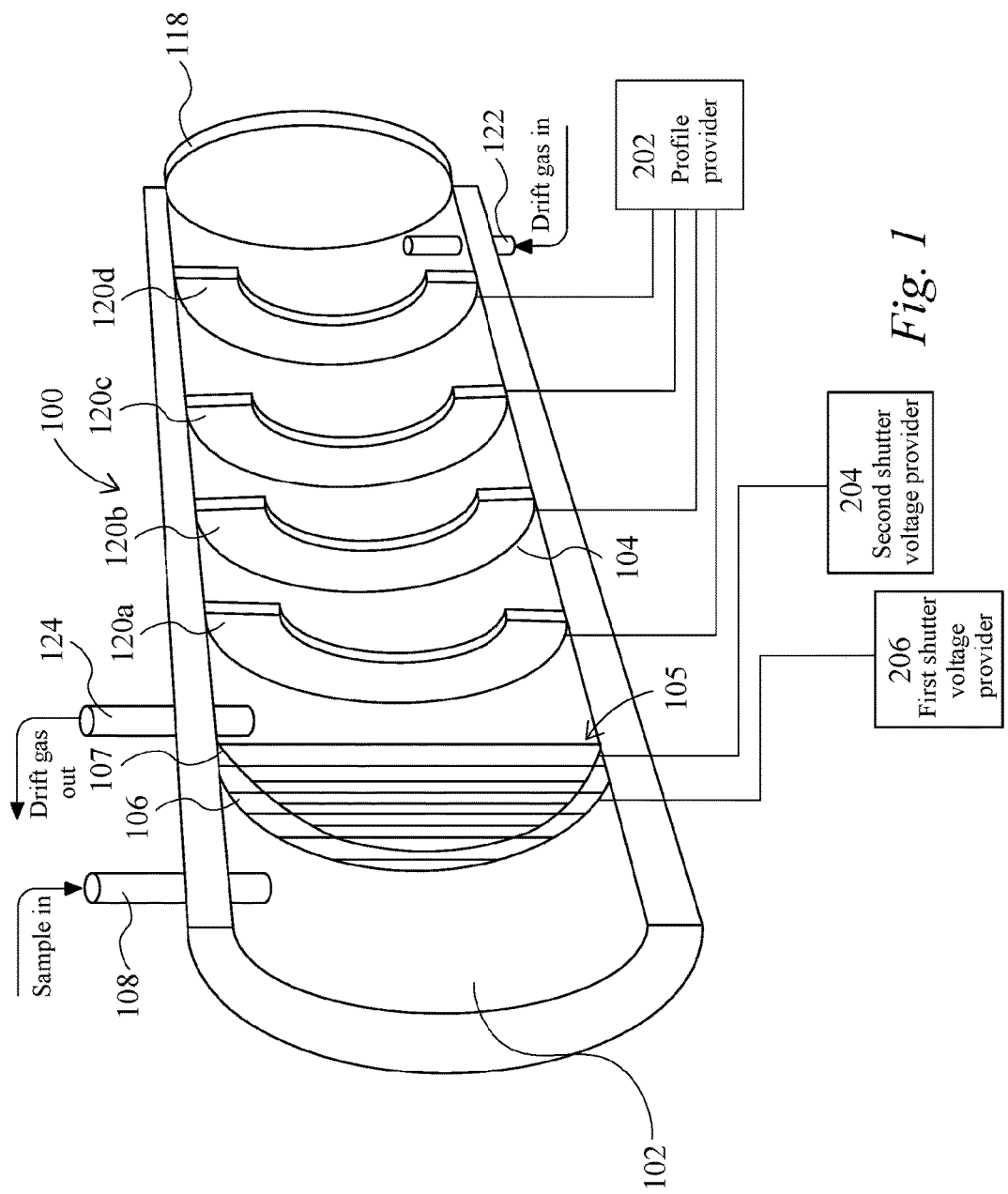
FIG. 1 is an illustration of a part section through an IMS cell.

FIG. 1 is an illustration of a part section through an IMS cell 100. The IMS cell comprises an ion shutter 105 comprising a first shutter electrode 106 and a second shutter electrode 107. A first shutter voltage provider 206 is configured to vary the first shutter electrode voltage, and a second shutter voltage provider 204 is configured to vary the second shutter electrode voltage. This enables a barrier voltage between the first shutter electrode 106 and the second shutter electrode 107 to be controlled by varying both the first shutter electrode voltage and the second shutter electrode voltage. This can be used to open and close the shutter 105 to provide a gating function that controls the admission of ions through the shutter.

In some embodiments the shutter electrodes 105 may be spaced apart in the direction of travel of the ions. In these embodiments, the voltage of the shutter that is nearest to the ions of interest (e.g. ions in the reaction region 102 prior to opening of the shutter, and in the drift region 104 after closing of the shutter) may be controlled to match the profile voltage in the IMS cell 100. This may enable ions in the reaction region to more closely approach the shutter 105 prior to its opening, and may reduce disturbances in the profile voltage in the drift chamber 104 due to closing of the shutter.

Other voltage control schemes may be applied to the shutter electrodes 105. In some schemes, opposing variations in the voltage of the first shutter electrode 106 and the second shutter electrode 107 are used to vary the barrier voltage. Such embodiments may at least partially avoid changes in the mean voltage of the shutter due to the action of opening and closing of the shutter 105. For example the electric field due to the shutter 105 at a point that is farther from the shutter than the spacing between conductors of the shutter may vary less than the change in barrier voltage would cause to be the case in the conventional case of using one fixed voltage electrode and one moving voltage electrode, for example the mean voltage of the shutter may remain constant, for example constant enough to avoid disturbances in the profile voltage. The shutter electrodes may be either coplanar or non-coplanar.

The shutter electrodes 106, 107 may each comprise elongate conductors, and the elongate conductors of the first shutter electrode 106 may be aligned in the drift direction with the elongate conductors of the second shutter electrode 107. The elongate conductors of each shutter electrode 106, 107 may be arranged as a grid, such as a mesh, for example a triangular, rectangular, hexagonal, or other regular or irregular mesh. As will be explained later, the shutter electrodes 106, 107 need not be separated in the drift direction. For example they may be coplanar, in which case the elongate conductors may be interdigitated, for example they may be interwoven.

The IMS cell of FIG. 1 includes a reaction region 102 for providing ions to the IMS cell. As illustrated, the IMS cell 100 includes an inlet 108 for enabling material to be introduced from a sample of interest to the reaction region 102. The reaction region 102 is separated from a drift region 104 by the ion shutter 105. In the example illustrated in FIG. 1, the drift region 104 lies between the reaction region 102 and a detector 118 such as a collector, for example a Faraday cup for detecting the arrival of ions, or another type of a detector 118 such as a mass spectrometer.

As illustrated a voltage profile provider 202 is arranged to provide a spatially varying voltage profile along the IMS cell 100. The voltage profile in the drift region 104 may be applied using a series of drift electrodes 120a, 120b, 120c and 120d spaced apart along the drift region 104. Although not illustrated in FIG. 1, a repeller plate or other electrode may be coupled to the profile provider 202 and arranged for extending this voltage profile into the reaction region 102. Between the reaction region 102 and the detector 118 the profile voltage varies spatially (e.g. as a function of displacement along the cell in the drift direction) to provide an electric field that moves ions along the cell 100 towards the detector 118.

The shutter 105 has two closed states. In a first one of the closed states, the voltage of the first shutter electrode 106 is controlled to match the profile voltage at the location of the first shutter electrode. In a second closed state the voltage of the second shutter electrode 107 is controlled to match the profile voltage at the location of the second shutter electrode. This can control the passage of ions of interest through the shutter 105 in a manner selected to reduce disturbances of the profile voltage around the ion shutter 105 (a) in the reaction region in the first closed state and (b) in the drift chamber in the second closed state. As explained below, the shutter may also have a reset state in which the voltage of neither shutter electrode matches the profile voltage.

In operation, a substance of interest is introduced to the reaction region where it can be ionised. With ions in the reaction region, the shutter 105 is held in the first closed state. To open the shutter 105 to release ions from the reaction region 102, the second shutter voltage provider 204 then matches the voltage of the second shutter electrode 107 to the profile voltage. To close the shutter after ions of interest have passed into the drift chamber, the shutter 105 is switched into its second closed state. An example of such operation will be described in greater detail below with reference to FIG. 2 and FIG. 3.

Figure 2:
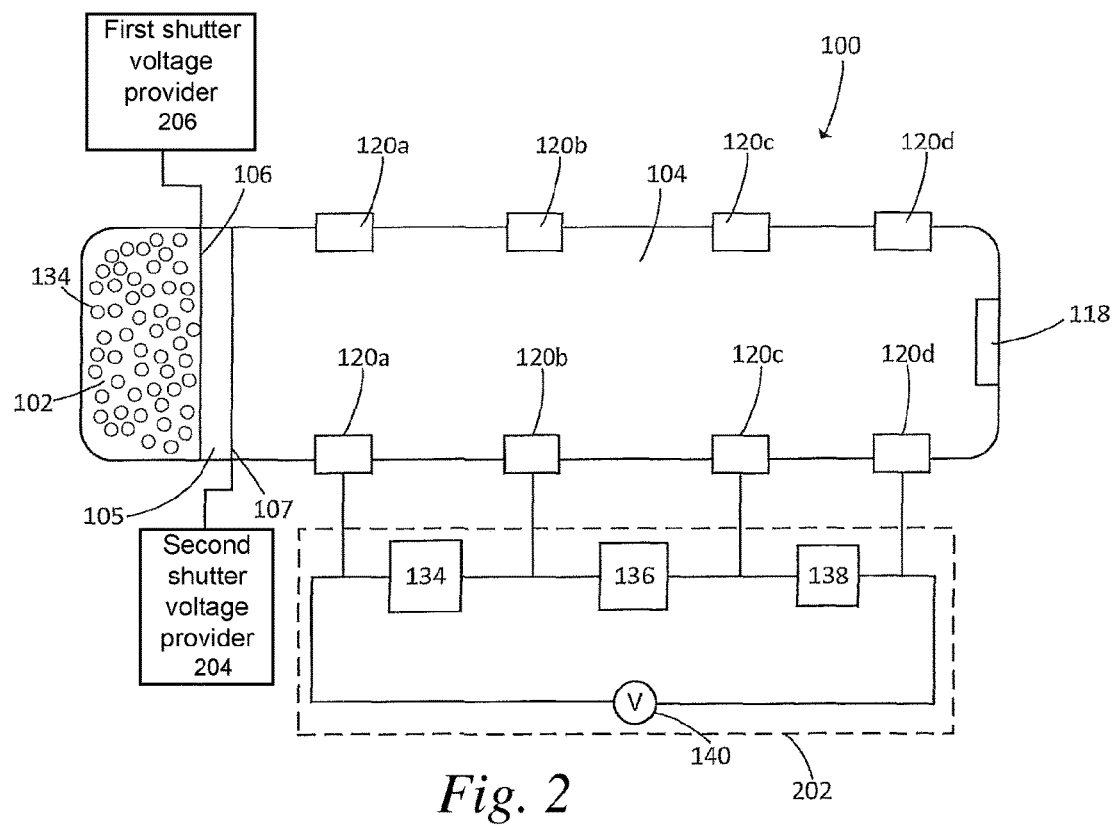
FIG. 2 shows a schematic diagram of an IMS cell such as that illustrated in FIG. 1.

Although not yet mentioned, it will be appreciated in the context of the present disclosure that the IMS cell 100 may be configured to provide a flow of drift gas in a direction generally opposite an ion's path of travel to the detector 118. For example, the drift gas can flow from adjacent the detector 118 toward the shutter 106. As illustrated, a drift gas inlet 122 and drift gas outlet 124 can be used to pass drift gas through the drift region. Example drift gases include, but are not limited to, nitrogen, helium, air, air that is re-circulated (e.g., air that is cleaned and/or dried) and so forth. Drift electrodes 120a, 120b, 120c and 120d may be arranged to guide ions toward detector 118, for example the drift electrodes 120a, 120b, 120c and 120d may comprise rings which may be arranged around the drift region 104 to move ions onto the detector 118. Although the example of FIG. 1 includes only four drift electrodes 120a, 120b, 120c and 120d in some examples a greater or lesser number of drift electrodes may be used, for example, a single drift electrode may be used in combination with the detector 118 to apply an electric field to guide ions toward the detector 118. FIG. 2 shows an example of a voltage profile provider coupled to the first drift electrode 120a, second drift electrode 120b, third drift electrode 120c and fourth drift electrode 120d. In an example the voltage on the drift electrodes 120a, 120b, 120c and 120d is such that the profile voltage varies linearly with distance along the IMS cell, for example having a constant gradient of voltage with distance in the drift region from the ion shutter to the detector 118. Other examples of voltage profiles may be used. In the example shown in FIG. 2 the profile provider comprises a potential divider. In the example illustrated in FIG. 2, the potential divider of the profile provider comprises a power provider 140 and a first resistor 134 coupling first drift electrode 120a and second drift electrode 120b, a second resistor 136 coupling second drift electrode 120b and third drift electrode 120c, and a third resistor 138 coupling third drift electrode 120c and fourth drift electrode 120d. The first resistor 134, the second resistor 136, and the third resistor 138 are coupled in series to the power provider 140 to form the potential divider. Other examples of voltage providers may be used, for example active rather than passive, resistive, components may be arranged to control the voltages on the drift electrodes.

FIG. 2 also illustrates an example of an IMS cell having a first shutter electrode 106 and a second shutter electrode 107 that are non-coplanar. For example, they are spaced apart in the drift direction of the IMS cell—e.g. in the direction of travel of the ions from the reaction region towards the detector 118.

As shown, the first shutter electrode 106 is coupled to first shutter voltage provider 206 and the second shutter electrode 107 is coupled to second shutter voltage provider 204. In the example shown in FIG. 2 the ion shutter 105 is closed and ions of interest 134 are located in the reaction region 102. To hold the shutter closed, the second shutter voltage provider 204 is configured to control the second shutter electrode to differ from the profile voltage so that a barrier voltage between the first shutter electrode and the second shutter electrode inhibits the passage of ions through the shutter 105. The first shutter voltage provider 206 however is configured to match the first shutter electrode voltage to the profile voltage at the location of the first shutter electrode 106. This is significant because prior to opening of the shutter, the ions of interest 134 may be screened from the second shutter electrode 107 by the first shutter electrode 107. This may avoid a situation in which a region adjacent the shutter is depleted of ions when the shutter is closed.

This can reduce the time interval for which the shutter must be held open to allow passage of ions through the shutter.

FIG. 3a, FIG. 3b, FIG. 3c, FIG. 3d and FIG. 3e show sequential steps in a method of releasing ions 134 from a reaction region 102 to a drift region 104 of an IMS cell 100 such as that illustrated in FIG. 1 and FIG. 2.

Figure 3A:
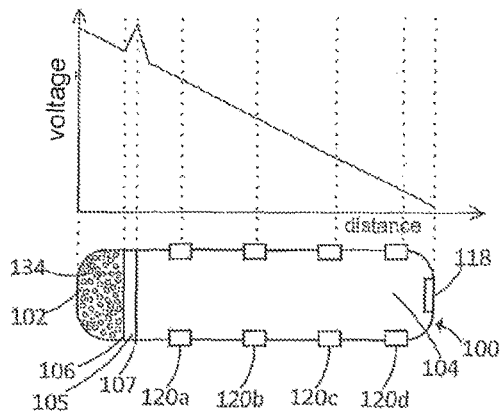
FIG. 3a shows a state prior to the release of ions into the drift region.

FIG. 3a shows the IMS cell 100 before the ions have been released into the drift region 104, this is an example of the situation illustrated in FIG. 2. In FIG. 3a, the ions 134 are held in the reaction region by the shutter 105. As described above with reference to FIG. 2 in this first closed state, the first shutter electrode 106 matches the profile voltage and screens the ions of interest from the second shutter electrode 107. Meanwhile, the second shutter electrode provides the barrier voltage.

In the example illustrated in FIG. 3a, the second shutter electrode 107 voltage is different from the voltage at the location of the second shutter electrode 107 on the voltage profile to create a barrier voltage to inhibit ions from passing the shutter 105. The barrier voltage in this configuration also inhibits ions of interest 134 from entering the region between the first shutter electrode and the second shutter electrode.

In the state, illustrated in FIG. 3a the first shutter electrode 106 shields the reaction region from the voltage on the second shutter electrode 107. Applying a voltage to the first shutter electrode 106 that matches the profile voltage can therefore enable the profile voltage to be maintained in the reaction region irrespective of the voltage applied to the second shutter electrode 107. This reduces perturbations in the electric field in the reaction region and reduces the depletion of ions in the vicinity of the ion shutter 105 in the reaction region 102.

Figure 3B:
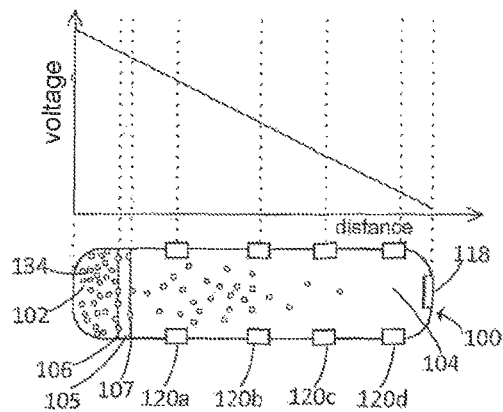
FIG. 3b shows a the release of ions into the drift region.

FIG. 3b shows the IMS cell 100 with the ion shutter 105 open to allow ions to move from the reaction region 102 to the drift region 104. The ion shutter is opened by applying a voltage to the first shutter electrode 106 and the second shutter electrode 107 that matches the profile voltage at the location of each respective shutter electrode.

The ion shutter remains in the open state shown in FIG. 3b for a short period of time to release a packet of ions. The period of time that the ion shutter remains open determines the spread of start times of the group of ions (e.g. the time at which each ion in the group actually passes the shutter). For example, if the ion shutter remains open for a period of time, some ions will have passed the shutter very soon after it was opened, and some ions would pass through immediately before it was shut—the resulting group of ions may have a distribution in start times and the ability of the IMS cell to resolve differences in time of flight is reduced as a result. The inventor has appreciated that if the barrier voltage encroaches on the reaction region (e.g. if the presence of the barrier voltage causes the voltage in the reaction region to differ from the profile voltage) this may cause a space adjacent the shutter to be depleted of ions. This depletion region may require the shutter to be open for an even longer period of time than would otherwise be required because ions in the reaction region would also have to travel across the depletion region.

In the first closed state illustrated in FIG. 3a however, the first shutter electrode matches the profile voltage, and screens the reaction region from the second shutter electrode. In the open state illustrated in FIG. 3b, the first shutter electrode 106 voltage is the same as its voltage in the first closed state illustrated in FIG. 3a. Therefore there is little or no perturbation in the electric field in the reaction region 102 associated with opening of the ion shutter. The reaction region 102 may be shielded from the effect of the second shutter electrode. This is significant because it may reduce the degree to which the barrier voltage intrudes into the reaction region. Embodiments may avoid depleting the number of ions in the space adjacent the shutter in the reaction region. This can enable the shutter to be opened for shorter intervals of time than might be the case if ions had first to traverse a depletion region adjacent to the shutter before they could pass into the drift region.

Figure 3C:
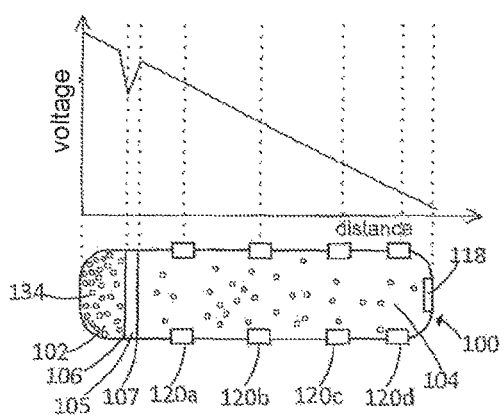
FIG. 3c shows the ion shutter being shut.

As illustrated in FIG. 3c once a group of ions has passed into the drift region 104, the ion shutter can be closed. This can be done by changing the first shutter electrode 106 voltage so that it is different from the profile voltage while the second shutter electrode is matched to the profile voltage. This provides a barrier voltage to stop further ions moving from the reaction region 102 to the drift region 104. In this second closed state, the second shutter electrode 107 screens the group of ions in the drift chamber from the first shutter electrode 106 and matches the profile voltage at its own location. The voltage profile in the drift region 104 is therefore less perturbed by the action of closing the shutter 106, 107, this can reduce the possibility that different ions experience different electric fields in the same parts of the drift region 104.

After a selected time interval in this second closed state, the ion shutter is reset. This time interval may be selected to provide a sufficient amount of time for the low mobility ions to travel to a part of the drift chamber in which the electric field matches the profile voltage, for example a part of the drift chamber in which the difference from the profile voltage due to the second shutter is much less than the profile voltage, for example so that the effect of this difference on time of flight of the ions is not measurable at the operating resolution of the IMS cell. This time may be selected based on the time of flight to the drift electrode 120a that is closest to the second shutter. Other, longer, times may also be used, for example long enough to allow the ions of interest to travel the length of the drift chamber. For example the time interval may be selected based on the cycle time of the IMS cell, and/or based on the longest expected time taken for ions of interest to reach the detector 118.

Figure 3D:
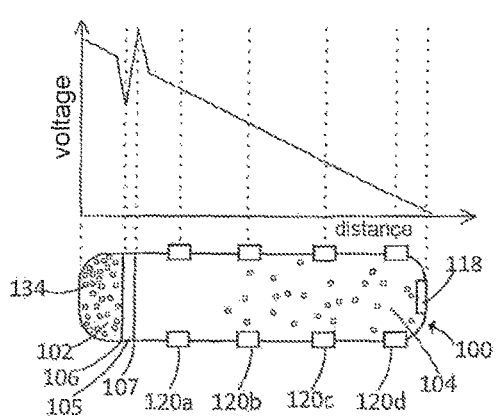
FIG. 3d shows a first step of resetting the ion shutter.

As illustrated in FIG. 3d the shutter 105 can then be reset by increasing the voltage on the second shutter electrode relative to the voltage applied in the second closed configuration illustrated in FIG. 3c. As a result, the voltage on the second shutter electrode 107 is greater than the profile voltage at the position of the second shutter electrode. In this first step of the reset operation, the voltage on the first shutter electrode 106 remains at the voltage that it was at in the second closed state illustrated in FIG. 3c, e.g. at a voltage offset from (e.g. lower than) the profile voltage at the location of the first shutter electrode.

Figure 3E:
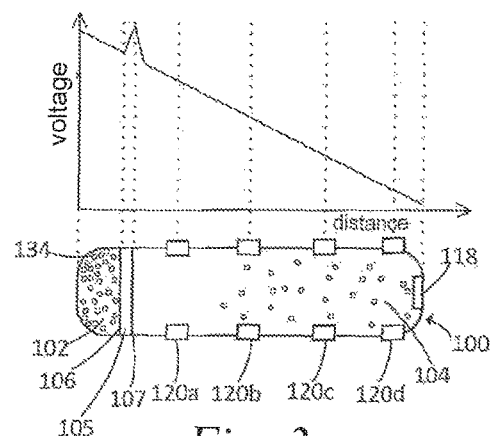
FIG. 3e shows a second step of resetting the ion shutter.

FIG. 3e illustrates a second step in the reset of the ion shutter. In this second step of the reset process, the voltage on the first shutter electrode 106 is matched to the profile voltage at the location of the first shutter electrode 106. The voltage on the second shutter electrode 107 remains at the voltage shown in FIG. 3d, a voltage greater than the voltage at the location of the second shutter electrode on the profile voltage. This returns the shutter to the first closed state without reducing the barrier voltage—for example, during the process of returning the shutter to the first closed state the barrier voltage is increased. Embodiments may avoid inadvertent opening of the shutter when returning the shutter to its first closed state. The resulting voltage profile in the IMS cell after this second step of the reset is the same as that shown in FIG. 3a, and the IMS cell is ready to release another packet of ions into the drift region.

Figure 4A:
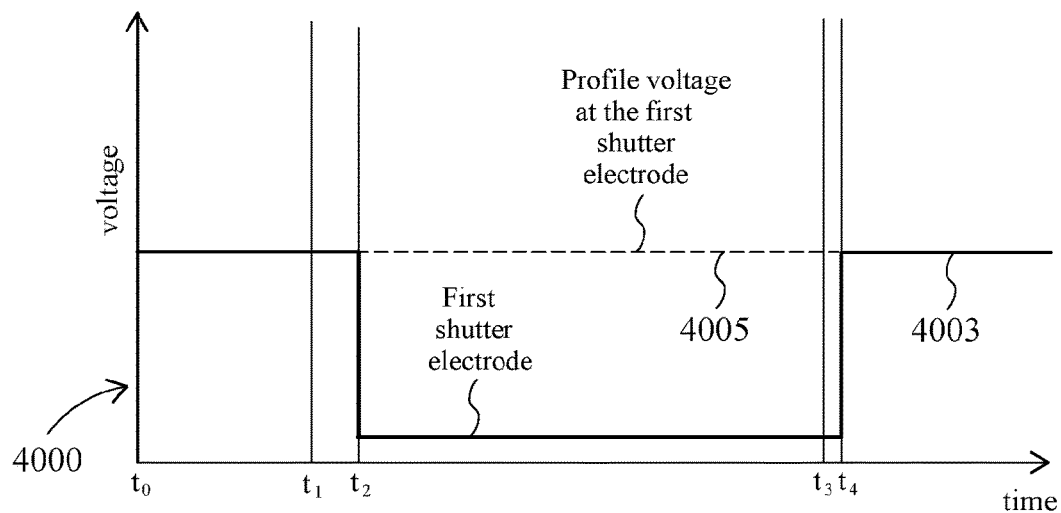
FIG. 4 illustrates a voltage control scheme for a shutter using two plots of changes in voltage as a function of time for the first shutter electrode (FIG. 4a) and the second shutter electrode (FIG. 4b)
Figure 4B:
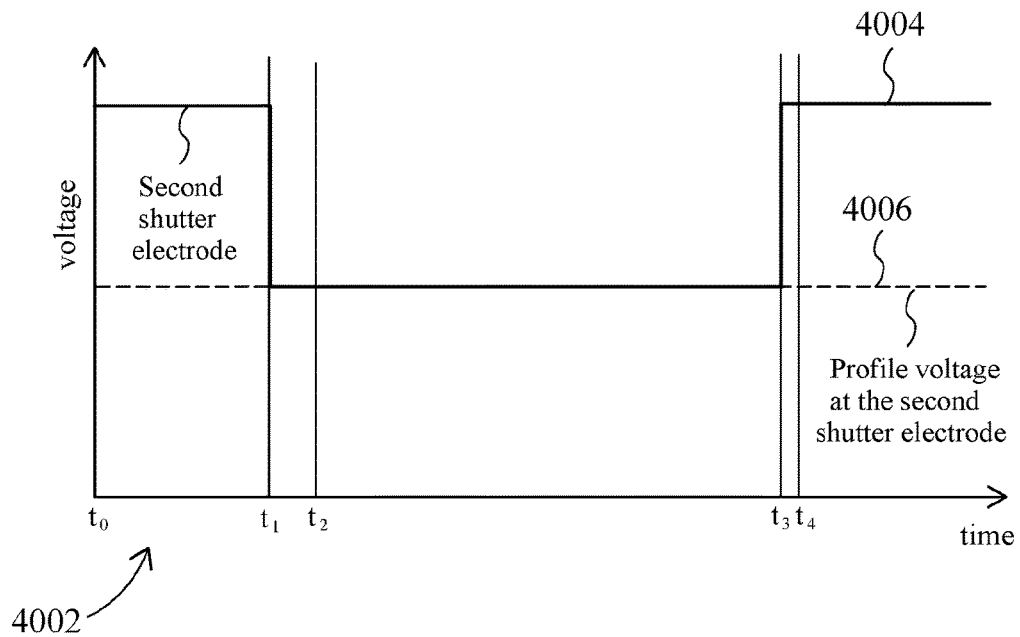

FIG. 4a and FIG. 4b show voltage plots 4000, 4002 that provide an example of a method of controlling an ion shutter. The method comprises controlling a barrier voltage between the first shutter electrode and the second shutter electrode by varying both the voltage of the first shutter electrode and the voltage of the second shutter electrode.

FIG. 4a illustrates a plot 4000 of voltage against time for a first shutter electrode for a shutter such as that illustrated in FIG. 1, FIG. 2, or FIG. 3. FIG. 4b illustrates a plot 4002 of voltage against time for a second such shutter electrode. FIG. 4a and FIG. 4b show a dotted line indicating the profile voltage as a dotted line 4005, 4006. This dotted line 4005, 4006 indicates the spatially varying profile voltage at the location of the first shutter electrode 4005 and the second shutter electrode 4006 respectively (the first in 4a, the second on 4b). In each case, the shutter electrode voltage (the first 106 in 4a, the second 107 on 4b) is shown as a heavy unbroken line 4003, 4004.

The example illustrated in FIG. 4a and FIG. 4b is one example of a method in which the first shutter electrode and the second shutter electrode are spaced apart in the drift direction, and the voltage of the shutter electrode that is closest to the ions of interest is controlled to match the profile voltage. Matching may comprise being set to the same voltage, for example matching may comprise being offset by less than a selected voltage tolerance, for example matching may comprise being sufficiently equal to the profile voltage that unwanted perturbations of the ions are not measurable.

The method illustrated in FIG. 4a and FIG. 4b comprises controlling the voltage of the shutter electrode that is furthest from the ions of interest to be different from the profile voltage to provide the barrier voltage. For example if the ions of interest are in the reaction region (period $t_0$ to $t_1$) the first shutter electrode voltage matches the profile voltage. During this period, a barrier voltage is provided by controlling the second shutter electrode voltage to be different from the profile voltage. This is the first closed state of the shutter. As illustrated in FIG. 4b, at time $t_1$ the second shutter electrode is matched to the profile voltage. This opens the shutter to allow ions to pass because both the shutter electrodes match the profile voltage—the barrier voltage is removed.

A group of ions of interest is thus released to travel from the reaction region, through the open shutter. To close the shutter again behind this group, at time $t_2$, the first shutter electrode is changed from the profile voltage while the second shutter remains at the profile voltage. The shutter may remain in this second closed state for an interval, $t_2$ to $t_3$, selected to be long enough to allow the ions of interest to travel to a part of the drift chamber in which the electric field matches the profile voltage, for example a part of the drift chamber in which the difference from the profile voltage due to the second shutter is much less than the profile voltage, for example so that the effect of this difference on time of flight of the ions is not measurable. This time may be selected based on the time of flight to the drift electrode 120a that is closest to the second shutter. Other, longer, times may also be used, for example long enough to allow the ions of interest to travel the length of the drift chamber.

The shutter may then be reset from the second closed state, at time $t_3$, by increasing the barrier voltage. For example, the second shutter electrode voltage may be changed to increase the barrier voltage. The first shutter electrode voltage may be changed less than the second electrode voltage while doing this, for example it may be held constant as illustrated during the period $t_3$ to $t_4$ illustrated in FIG. 4a.

It will be appreciated that FIG. 4 illustrates one possible voltage control scheme that can provide the sequence of events illustrated in FIG. 3. For example—the configuration in FIG. 3a may correspond to the time interval $t_0$ to $t_1$. The configuration shown in FIG. 3b may correspond to the time interval $t_1$ to $t_2$. The configuration shown in FIG. 3c may correspond to the time interval $t_2$ to $t_3$. The configuration shown in FIG. 3d may correspond to the time interval $t_3$ to $t_4$. And the configuration shown in FIG. 3e may correspond to time $t_4$ onwards. It will be appreciated however that although square edged pulses (rather like a box-car waveform) are illustrated in FIG. 4, more gradually varying voltages may be used. For example the voltage transitions may be gradual, for example ramped, for example rolled off. It will also be appreciated that because square pulses have been used for this illustration it appears that the voltage of the shutter electrodes may be held constant between transitions, but this is not necessarily the case. As a result the voltage waveforms on the electrodes may comprise at least partial admixtures of at least one of trapezoidal pulses, square pulses, triangular pulses, and quasi-sinusoidal lobes. The voltage pulses need not be symmetric—for example the voltage excursion of the first shutter electrode may be greater or less than the voltage excursion of the second shutter electrode.

FIG. 5 illustrates an alternative voltage control scheme that can be used with a variety of shutter arrangements, for example the first shutter electrode spaced apart from the second shutter electrode in the drift direction of the IMS cell, or the first shutter electrode being coplanar with the second shutter electrode. In the example illustrated in FIG. 5, the barrier voltage is controlled by providing opposing variations in the voltage of the first shutter electrode and the second shutter electrode. That is to say, when the voltage of the first shutter electrode is increased, the voltage of the second shutter electrode is decreased and vice versa. The relative sizes of the voltage excursions of the two shutters may be chosen so that they at least partially cancel each other out—this may reduce, for example avoid, changes in the average voltage of the shutter as a whole as the shutter is opened and/or closed. These opposing variations may be centred on the profile voltage at the location of the shutter.

Figure 5A:
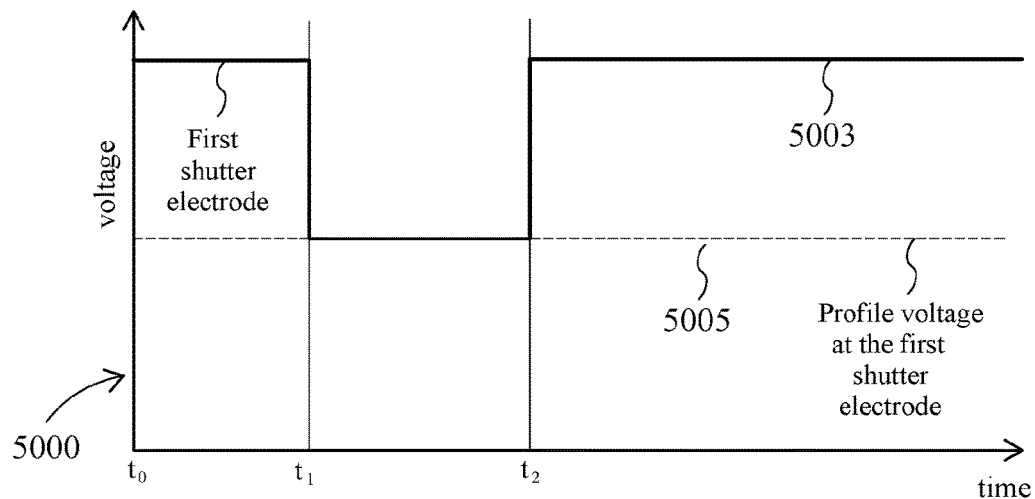
FIG. 5 illustrates another voltage control scheme for a shutter using two plots of changes in voltage as a function of time for the first shutter electrode (FIG. 5a) and the second shutter electrode (FIG. 5b)
Figure 5B:
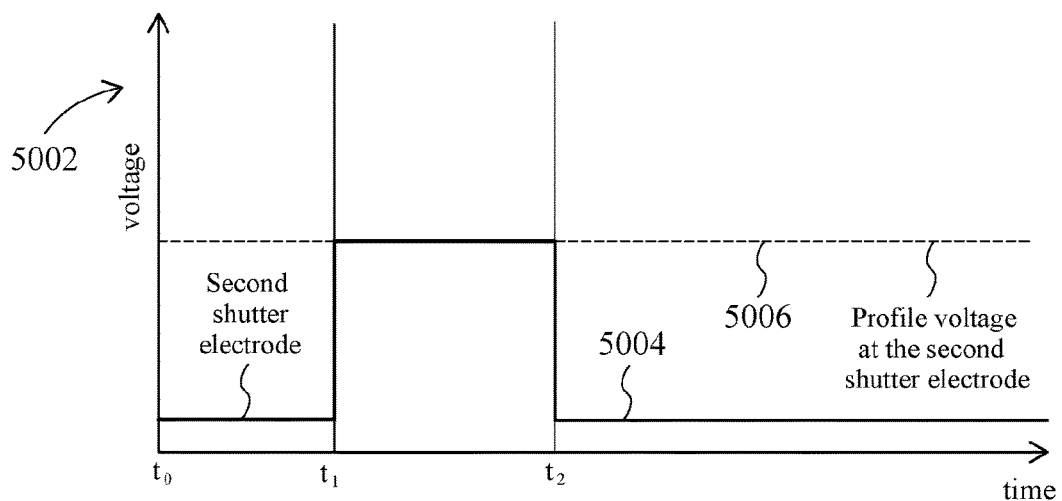

The plots in FIG. 5a and FIG. 5b use the same convention as in FIG. 4 in that the profile voltage at the location of each shutter electrode is illustrated as a dotted line 5005, 5006, and the relevant shutter electrode voltages are shown as a heavy unbroken line.

As shown in FIG. 5a, and FIG. 5b, while the shutter is closed between times $t_0$ and $t_1$ the first shutter electrode voltage is higher than the local profile voltage, and the second shutter electrode voltage is lower than the local profile voltage. This provides a barrier voltage between the two electrodes, but the average voltage of the two electrodes taken together differs from the profile voltage by less than the barrier voltage. For example, if the differences from the profile voltage are equal and opposite then the average voltage of the shutter may be equal to the profile voltage. To open the shutter, the voltages of both electrodes can be changed to reduce the barrier voltage—for example both shutter electrode voltages may be moved towards the local profile voltage. Later, to close the shutter again, the first shutter voltage can be increased and the second shutter electrode voltage decreased.

By making opposing variations in this way, the average voltage of the shutter may change by less than the change in barrier voltage when opening and closing the shutter. For example, the changes on the individual shutter electrodes may at least partially cancel each other out.

These different voltage control schemes may be used with a variety of different configurations of shutter. FIG. 6 illustrates an ion shutter for an IMS cell. The shutter shown in FIG. 6A comprises a first shutter electrode 106 and a second shutter electrode 107. As illustrated each of the first and second shutter electrodes 106, 107 comprise elongate conductive elements. In the interests of clarity, in this schematic drawing the conductors of the shutter electrodes are shown as if they are interdigitated, so that both can be clearly seen when looking at the face of the shutter—for example looking at it along the drift direction. It will be appreciated however that other arrangements of the shutter electrodes are possible. Indeed, not only the conductive elements, but the shutter electrodes themselves, may be arranged in a variety of different ways.

FIG. 6b, FIG. 6c, and FIG. 6d illustrate different possible arrangements. Each of these represents a section through a shutter such as that illustrated in FIG. 6A, transverse to the conductors. In the first of these, FIG. 6B, it can be seen that the first shutter electrode may be spaced apart from the second shutter electrode in a drift direction of the IMS cell (e.g. transverse to the major dimension of the shutter). The elongate conductive elements which make up the first shutter electrode may be aligned with those of the second shutter electrode along the drift direction (that is to say not offset transverse to the drift direction). In this configuration, viewed along the axis of the IMS cell, the conductors of first and second shutter electrode may be aligned so that one is hidden by the other.

As illustrated in FIG. 6, the elongate conductors of the shutter electrodes 106, 107 are straight. It will be appreciated however that such conductors may be arranged in other configurations. For example, the elongate conductors of each shutter electrode 106, 107 may be arranged as a grid, such as a mesh, for example a triangular, rectangular, hexagonal, or other regular or irregular mesh.

It is not however necessary that all shutters of the present disclosure have this arrangement. For example, the methods and apparatus described above with reference to FIG. 1, FIG. 2, FIG. 3, and FIG. 4, may also be implemented using shutters in which the shutter electrodes are offset but the elongate conductors are not aligned, for example as illustrated in FIG. 6c. For example they may be interdigitated and at least partially non coplanar, for example spaced apart in the drift direction.

As illustrated in FIG. 6d, the first shutter electrode and the second shutter electrode may also be coplanar, and this may be of particular utility when control schemes such as that illustrated in FIGS. 5a and 5b are used although this is not mandatory.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit. For example the voltage providers may be provided by a single drive circuit having multiple output channels, or separate drive circuitry may be provided for each. The voltage providers may comprise amplifiers arranged to provide switchable voltages, which may be fixed or arranged to vary relative to particular reference voltages. For example, the profile voltage of the IMS cell may be used as a reference voltage of the voltage providers which drive the shutter electrodes. The voltage providers described herein may comprise an AC power supply, which may comprise one or more step-up or step down transformers, the voltage providers may also comprise DC power supplies such as batteries or fuel cells or capacitive power stores. Combinations of AC and DC power may be used and the voltage provider may comprise an inverter for providing an AC voltage based on a DC power supply. In some embodiments the voltage providers may comprise rectifiers for providing DC voltage based on an AC power supply. Any combination of AC and DC power supply and voltage providing components may be used. In some embodiments the voltage provider may also operate as a current source.

Although in the above examples the ion shutter is illustrated between the reaction region and the drift chamber, a shutter may also be provided in place of, or to couple the IMS cell to a detector. This may permit operation of the shutter to select ions of particular mobilities (e.g. having particular time of flight along the cell). This can enable ions to be filtered before they are provided to a detector such as a mass spectrometer.

Where reference is made to electrodes it will be appreciated that any arrangement of conductors may be used, for example electrodes may comprise metals or other conductors and may be at least partially exposed and/or partially insulated.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. A method of controlling an ion shutter of an IMS cell, the method comprising:
controlling a barrier voltage between a first shutter electrode and a second shutter electrode to open and close the shutter to allow ions of interest to pass through the shutter in a drift direction by varying the voltage of the first shutter electrode; and varying the voltage of the second shutter electrode;
wherein the voltages of the first shutter electrode and the second shutter electrode are varied with respect to a spatially varying profile voltage of the IMS cell, the voltage of the first shutter electrode is controlled to match the profile voltage prior to opening of the shutter, and the first shutter electrode lies between a reaction region of the IMS cell and the second shutter electrode.

2. The method of claim 1, further comprising controlling the voltage of one of: the first shutter electrode or the second shutter electrode, based at least in part on the electrode closest to ions of interest that match the profile voltage.

3. The method of claim 2, further comprising controlling the voltage of the other one of the first shutter electrode and the second shutter electrode, that is furthest from the ions of interest, to be different from the profile voltage to provide the barrier voltage.

4. An IMS cell comprising:
an ion shutter comprising a first shutter electrode and a second shutter electrode;
a first shutter voltage provider circuit configured to vary the voltage of the first shutter electrode; and
a second shutter voltage provider circuit configured to vary the voltage of the second shutter electrode,
wherein the first shutter voltage provider circuit and the second shutter voltage provider circuit are configured to control a barrier voltage between the first shutter electrode and the second shutter electrode by varying the voltage of the first shutter electrode and the voltage of the second shutter electrode thereby to control the passage of ions of interest through the ion shutter in a drift direction; and
wherein the first shutter electrode lies between a reaction region of the IMS cell and the second shutter electrode, and the first shutter voltage provider circuit is configured to match the voltage of the first shutter electrode to a spatially varying profile voltage of the IMS cell prior to opening of the ion shutter.

5. The IMS cell of claim 4, wherein each of the first shutter electrode and second shutter electrode comprises elongate conductors, and wherein the elongate conductors of the first and second shutter electrodes are aligned in the drift direction.

6. The IMS cell of claim 4, wherein an ion drift region of the IMS cell is arranged to provide the ions of interest to a mass spectrometer.

7. The IMS cell of claim 4 wherein the second shutter voltage provider circuit opens the shutter by matching the voltage of the second shutter electrode to the profile voltage.

8. The IMS cell of claim 4, wherein the first shutter voltage provider circuit closes the shutter by controlling the voltage of the first shutter to be different from the profile voltage to provide the barrier voltage.

9. The IMS cell of claim 8 wherein the second shutter voltage provider circuit matches the voltage of the second shutter electrode to the profile voltage after the ion shutter is closed.

10. The IMS cell of claim 9 wherein the first shutter voltage provider circuit and the second shutter voltage provider circuit reset the shutter by changing the voltage of the second shutter electrode to increase the barrier voltage before returning the voltage of the first shutter electrode to the profile voltage.

11. A control apparatus for an IMS cell comprising:
a first shutter voltage provider circuit for varying the voltage of a first shutter electrode of an ion shutter; and
a second shutter voltage provider circuit for varying the voltage of a second shutter electrode of the ion shutter, wherein:
the first shutter voltage provider circuit is configured to match the first shutter electrode voltage to a profile voltage of the IMS cell prior to opening of the ion shutter;
the second shutter voltage provider circuit is configured to open the ion shutter by matching the second shutter electrode voltage to the profile voltage; and
the first shutter voltage provider circuit is configured to provide a barrier voltage to close the ion shutter by controlling the first shutter voltage to be different from the profile voltage to provide a barrier voltage.

12. A method of controlling an ion shutter of an IMS cell, the method comprising controlling a barrier voltage between a first shutter electrode and a second shutter electrode to open and close the shutter to allow ions of interest to pass through the shutter in a drift direction by varying the voltage of the first shutter electrode; and varying the voltage of the second shutter electrode;
wherein the voltages of the first shutter electrode and the second shutter electrode are varied with respect to a spatially varying profile voltage of the IMS cell; the method further comprising:
providing a voltage of the first shutter electrode which matches the profile voltage and providing a voltage of the second shutter electrode which is different from the profile voltage to close the shutter;
providing a voltage to both the shutter electrodes that matches the profile voltage to open the shutter; and
providing a voltage of the first shutter electrode that is different from the profile voltage while the voltage of the second shutter electrode matches the profile voltage to close the shutter.

13. An IMS cell comprising:
an ion shutter comprising a first shutter electrode and a second shutter electrode;
a first shutter voltage provider circuit configured to vary the voltage of the first shutter electrode; and
a second shutter voltage provider circuit configured to vary the voltage of the second shutter electrode,
wherein the first shutter voltage provider circuit and the second shutter voltage provider circuit are configured to control a barrier voltage between the first shutter electrode and the second shutter electrode by varying the voltage of the first shutter electrode and the voltage of the second shutter electrode thereby to control the passage of ions of interest through the ion shutter in a drift direction, wherein the first shutter electrode and the second shutter electrode are coplanar.

14. The IMS cell of claim 13 wherein each of the first shutter electrode and the second shutter electrode comprises a plurality of elongate conductors which are interdigitated.

\* \* \* \* \*